United States Patent [19]

Melnikov et al.

[11] 4,188,382
[45] Feb. 12, 1980

[54] THIAZOLINYL (THIAZOLYL) PHOSPHONAMIDATES AND PHOSPHORAMIDATES PESTICIDAL AND HERBICIDAL COMPOSITIONS BASED THEREON

[75] Inventors: Nikolai N. Melnikov; Artur F. Grapov; Ljudmila V. Razvodovskaya; Petr V. Popov; Aelita S. Sedykh; Galina K. Shapovalova; Galina M. Abelentseva; Tamara A. Siforova; Tatyana A. Nikolaeva; Valentina V. Galitsina; Leonid D. Stonov; Ljudmila A. Bakumenko, all of Moscow, U.S.S.R.

[73] Assignee: Vsesojuzny Nauchno, et al., Moscow, U.S.S.R.

[21] Appl. No.: 772,276

[22] Filed: Feb. 25, 1977

[51] Int. Cl.² .......................... C07F 9/65; A01N 9/36
[52] U.S. Cl. ........................ 424/200; 71/87; 548/115
[58] Field of Search ............ 260/306.7 E, 306.8 R; 424/200; 71/90, 87

[56] References Cited

U.S. PATENT DOCUMENTS

| | | | |
|---|---|---|---|
| 3,694,451 | 9/1972 | Mihailovski | 260/306.7 E |
| 3,723,450 | 3/1973 | Fancher | 260/306.8 R |
| 3,876,781 | 4/1975 | Gaughan | 424/200 |

FOREIGN PATENT DOCUMENTS

| | | | |
|---|---|---|---|
| 642765 | 7/1964 | Belgium | 260/306.7 E |
| 674102 | 4/1966 | Belgium | 260/306.7 E |
| 2316185 | 10/1974 | Fed. Rep. of Germany | 424/200 |

*Primary Examiner*—Alton D. Rollins
*Assistant Examiner*—Diana G. Rivers
*Attorney, Agent, or Firm*—Lackenbach, Lilling & Siegel

[57] ABSTRACT

Thiazolinyl (thiazolyl) phosphonamidates and phosphoramidates of the formula:

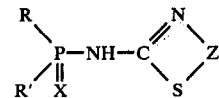

wherein R is a $C_1$-$C_4$-alkyl, a halo-$C_1$-$C_4$-alkyl, a $C_1$-$C_4$ alkoxy; R' is a $C_1$-$C_4$-alkoxy, phenoxy, a halophenoxy, a $C_1$-$C_4$-alkyl-amino, dialkylamino or thiazolinyl-2-amino; X is oxygen or sulphur; Z is —$CH_2$—$CH_2$— or —CH=CH— group which comprise an active principle for insecticidal, acaricidal and herbicidal compositions.

5 Claims, No Drawings

THIAZOLINYL (THIAZOLYL) PHOSPHONAMIDATES AND PHOSPHORAMIDATES PESTICIDAL AND HERBICIDAL COMPOSITIONS BASED THEREON

The present invention relates to thiazolinyl(thiazolyl) phosphonamidates and phosphoramidates and to insecticidal, acaricidal and herbicidal compositions based thereon.

Known from the literature are compounds of the formula:

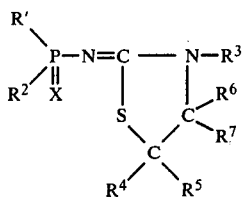

wherein
R' is an alkyl, alkoxy, or alkylthio;
$R^2$ is an alkyl, alkoxy, alkylthio, chloroalkyl, carboethoxy, alkylthio, chlorophenylthio, nitrobenzyloxy group; phenyl; a substituted phenoxy;
$R^3$ is an alkyl, benzyl, phenyl, an alkoxyalkyl, alkenyl, chloroalkenyl or 2-propinyl;
$R^4$ is hydrogen, alkyl, cyclohexyl, vinyl;
$R^5$, $R^6$ and $R^7$ is hydrogen or alkyl;
X is oxygen or sulphur (cf. U.S. Pat. Nos. 3,876,780; 3,876,781).

The prior art compounds feature a high insecticidal and acaricidal activity; however, they are active only against specific groups of insects and ticks, for example against the housefly and hairy mite.

It is an object of the present invention to provide novel efficient insecticides and acaricides possessing an enlarged spectrum of their effect and higher selectivity against quarantine agricultural vermin as well as to provide novel organophosphorus herbicides.

This object is accomplished by the preparation of compounds corresponding to formula (1)

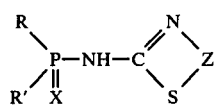 (1)

wherein
R is a $C_1$-$C_4$-alkyl, a halo-$C_1$-$C_4$-alkyl or $C_1$-$C_4$ alkoxy;
R' is a $C_1$-$C_4$ alkoxy, phenoxy, halophenoxy, a $C_1$-$C_4$-alkylamino, dialkylamino or thiazolinyl-2-amino;
X is oxygen or sulphur;
Z is —$CH_2$—$CH_2$—; —CH═CH—.

The compounds of formula (1) differ from conventional compounds by the presence of a mobile proton in the molecule and can exist in the form of a mixture of tautomers A and B:

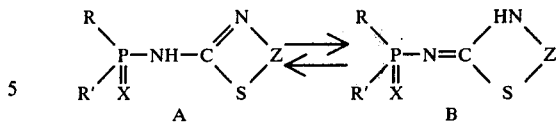

Typical compounds of formula (1) may be exemplified by the following substances:
O-Phenyl-N-thiazolinyl-2-methylphosphonamidate;
O-Ethyl-N-thiazolinyl-2-methylphosphonamidate;
O-Butyl-N-thiazolinyl-2-amidomethylphosphonate;
O-4-Chlorophenyl-N-thiazolinyl-2-methylphosphonamidate;
O-2,4-Dichlorophenyl-N-thiazolinyl-2-methylphosphonamidate;
O-Methyl-N-thiazolinyl-2-methylphosphonamidothioate;
O-Ethyl-N-thiazolinyl-2-methylphosphonamidothioate;
O-Butyl-N-thiazolinyl-2-methylphosphonamidothioate;
O-Phenyl-N-thiazolinyl-2-methylphosphonamidothioate;
O-4-Chlorophenyl-N-thiazolinyl-2-methylphosphonamidothioate;
O-2,4-Dichlorophenyl-N-thiazolinyl-2-methylphosphonamidothioate;
O-2,4,5-Trichlorophenyl-N-thiazolinyl-2-methylphosphonamidothioate;
O-2,4-Dichlorophenyl-N-thiazolinyl-2-chloromethylphosphonamidothioate;
O-Ethyl-N-thiazolinyl-2-chloromethylphosphonamidothioate;
O-Ethyl-N-thiazolinyl-2-chloroethylphosphonamidothioate;
N,N-Diethylamido-N'-thiazolinyl-2-methylphosphonamidothioate;
O-Methyl-O-phenyl-N-thiazolinyl-2-methylphosphonamidothioate;
O-Butyl-O-phenyl-N-thiazolinyl-2-methylphosphonamidothioate;
O-Methyl-N-thiazolyl-2methylphosphonamidate;
O-Butyl-N-thiazolyl-2-methylphosphonamidate;
O-Ethyl-O-phenyl-N-thiazolyl-2-phosphonamidothioate;
O-Phenyl-N-thiazolyl-2-methylphosphonamidate;
O-4-Chlorophenyl-N-thiazolyl-2-methylphosphonamidate;
O-4-Chlorophenyl-N-thiazolyl-2-methylphosphonamidothioate;
O-Ethyl-N-thiazolyl-2-phenylphosphonamidate;
N,N'-Bis-(thiazolinyl-2-methylphosphonamidate;
N-Ethyl-N'-thiazolinyl-2-methylphosphonamidothioate.

In accordance with the present invention, a method for preparing said compounds of formula (1) resides in reacting a compound of the formula:

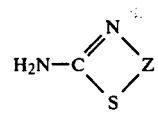

wherein Z is —$CH_2$—$CH_2$— or —CH═CH— group, with phosphonochloridates or phosphorochloridates of the formula:

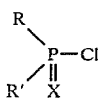

wherein

R is a $C_1$-$C_4$-alkyl, a halo-$C_1$-$C_4$-alkyl or a $C_1$-$C_4$ alkoxy;

R' is $C_1$-$C_4$ alkoxy, phenoxy, halophenoxy; $C_1$-$C_4$ alkyl amino, dialkylamino or thiazolinyl-2-amino;

X is oxygen or sulphur, in an inert organic solvent in the presence of an acceptor of hydrogen chloride.

As the organic solvent use can be made of alcohols, ketones, chlorinated hydrocarbons, esters and the like. As the acceptor of hydrogen chloride use may be made mainly of tertiary amines such as triethylamine, pyridine, collidine and the like.

Said components are employed in the stoichiometric ratio. The reaction proceeds under normal pressures with heating or without.

It has been found that the compounds of formula (1) listed hereinabove feature a pronounced insecticidal, acaricidal and herbicidal activity.

In accordance with the present invention, the insecticidal and acaricidal composition contains, as the active principle, a compound of the formula:

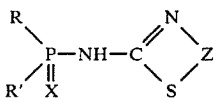

wherein

R is a $C_1$-$C_4$ alkyl, a halo-$C_1$-$C_4$-alkyl or $C_1$-$C_4$-alkoxy;

R' is a $C_1$-$C_4$-alkoxy; phenoxy; halophenoxy; a $C_1$-$C_4$ alkylamino, dialkylamino or thiazolinyl-2-amino;

X is oxygen or sulphur;

Z is —CH$_2$—CH$_2$— group, and an inert carrier therefor.

The most active insecticides and acaricides are the following compounds:

O-phenyl-N-thiazolinyl-2-methylphosphonamidate;
O-phenyl-N-thiazolinyl-2-methylphosphonamidothioate;
O-2,4,5-trichlorophenyl-N-thiazolinyl-2-methylphosphonamidothioate;
O-4-chlorophenyl-N-thiazolinyl-2-methylphosphonamidothioate.

Said compounds, in respect to their effectiveness against Colorado beetle are superior over chlorophos, bazudine, galecrone and benzophosphate; in respect to rice weevil they are similar, in their effect, to chlorophos; in respect to web mite these compounds are superior over galecrone and menazone.

The herbicidal composition according to the present invention contains, as an active principle, a compound of the formula

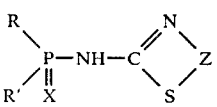

wherein

R is a $C_1$-$C_4$ alkyl, a halo-$C_1$-$C_4$-alkyl, or a $C_1$-$C_4$ alkoxy;

R' is a $C_1$-$C_4$-alkoxy, phenoxy, halophenoxy, $C_1$-$C_4$ alkylamino, dialkylamino or thiazolinyl-2-amino;

X is oxygen or sulphur;

Z is —CH$_2$—CH$_2$—, —CH=CH—, and an inert carrier therefor.

Most active herbicides are the following:
O-2,4-dichlorophenyl-N-thiazolinyl-2-chloromethylphosphonamidothioate;
O-2,4-dichlorophenyl-N-thiazolinyl-2-methylphosphonamidothioate.

The compounds of the formula (1) can be used individually or in a mixture with various carriers and additives. The carriers may be either solid or liquid substances which comprise conventional agents adapted for the above-mentioned purposes, for example solvents, dispersing agents, wetting agents, solid vehicles, binders and the like.

The compounds of formula (1) are employed mainly in the form of solutions, slurries, wettable powders and granules. Concentration of the active principle in said compositions ranges from 0.01 to 80%.

The compositions according to the present invention are prepared in a conventional manner by way of intermixing and/or crushing compounds of formula (1) with a carrier.

Thiazolinyl(thiazolyl)amides of phosphorus acids of formula (1) may be used as they are or in a mixture with other pesticides.

The present invention is further illustrated by the following specific Examples, wherefrom Examples 1 through 15 illustrate the method of preparing compounds according to the present invention, Example 16 illustrates preparation of the composition according to the present invention, while Examples 17 through 19 illustrate pesticidal and herbicidal properties thereof.

EXAMPLE 1

O-phenyl-N-thiazolinyl-2-methylphosphonamidate

To 3.4 g of O-phenylmethylphosphonic chloride in benzene there is dropwise added a solution of 1.8 g of 2-aminothiazoline and 2.5 ml of triethylamine in benzene upon cooling with ice. The mixture is allowed to stay overnight. Thereafter, triethylamine chlorohydrate is filtered off and the solvent is distilled off in vacuum. The residue is added with water; crystals are filtered off, washed with ether and twice recrystallized from acetone to give O-phenyl-N-thiazolinyl-2-methylphosphonamidate. The yield is 76%, melting point is 137°–138° C.

Found, %: N 10.78, 10.80; P 12.07, 11.85; S 12.76, 12.55; $C_{10}H_{13}N_2O_2PS$. Calculated, %; N 10.93; P 12.09; S 12.51.

EXAMPLE 2

O-phenyl-N-thiazolinyl-2-methylphosphonamidothioate

In a manner similar to that described in Example 1 hereinabove, from 2.6 g of O-phenylmethylphosphonic chloride, 1.3 g of 2-aminothiazoline and 2 ml of triethylamine O-phenyl-N-thiazolinyl-2-methylphosphonamidothioate is obtained at the yield of 28.8%; melting point is 130° to 130.5° C.

Found, %: 10.24, 10.25; P 10.75, 10.89. $C_{10}H_{13}N_2OPS_2$. Calculated, %: N 10.29; P 11.37.

EXAMPLE 3

O-4-chlorophenyl-N-thiazolinyl-2-methylphosphonamidate

In a manner similar to that described in the foregoing Example 1, from 5.3 g of O-4-chloromethylphosphonic chloride, 2.88 g of 2-aminothiazoline and 3.8 ml of triethylamine O-4-chlorophenyl-N-thiazolinyl-2-methylphosphonamidate is obtained with the yield of 71%; melting point is 122°–123.5° C.

Found, %: N 9.24, 9.30; P 10.86, 10.62; S 11.06, 11.26. $C_{10}H_{12}ClN_2O_2PS$. Calculated, %: N 9.64; P 10.65; S 11.03.

EXAMPLE 4

O-2,4-dichlorophenyl-N-thiazolinyl-2-methylphosphonamidothioate

In a manner similar to that described in the foregoing Example 1, from 6.8 g of O-2,4-dichlorophenylmethylthiophosphonic chloride, 2.5 g of 2-aminothiazoline and 3.5 ml of triethylamine there is obtained O-2,4-dichlorophenyl-N-thiazolinyl-2-methylphosphonamidothioate with yield of 55%, melting point 117°–118° C.

Found, %: N 8.29, 8.25; S 18.28, 19.07. $C_{10}H_{11}Cl_2N_2OPS_2$. Calculated, %: N 8.21; S 18.79.

EXAMPLE 5

O-2,4-dichlorophenyl-N-thiazolinyl-2-methylphosphonamidate

In a manner similar to that described in the foregoing Example 1, from 7.6 g of O-2,4-dichlorophenylmethylphosphonic chloride, 3 g of 2-aminothiazoline and 4.1 ml of triethylamino there is obtained O-2,4-dichlorophenyl-N-thiazolinyl-2-methylphosphonamidate with the yield of 18%, melting point 112°–113° C.

Found, %: N 8.15, 8.20; S 10.16, 9.83. $C_{10}H_{11}Cl_2N_2O_2PS$. Calculated, %: N 8.62; S 9.86.

EXAMPLE 6

O-2,4,5-trichlorophenyl-N-thiazolinyl-2-methylphosphonamidothioate

In a manner similar to that described in the foregoing Example 1, from 7.6 g of O-2,4,5-trichlorophenylmethylthiophosphonic chloride, 2.5 g of 2-aminothiazoline and 3.5 ml of triethylamine there is obtained O-2,4,5-trichlorophenyl-N-thiazolinyl-2-methylphosphonamidothioate at the yield of 31.4%, melting point of 124°–124.5° C.

Found, %: N 7.30, 7.31; P 8.04, 7.99; S 16.73, 16.54. $C_{10}H_{10}Cl_3N_2OPS_2$. Calculated, %: N 7.46; P 8.25; S 17.07.

EXAMPLE 7

O-2,4-dichlorophenyl-N-thiazolinyl-2-chloromethylphosphonamidothioate

In a manner similar to that described in Example 1 hereinbefore, from 7.7 g of O-2,4-dichlorophenylchloromethylthiophosphonic chloride, 2.5 g of 2-aminothiazoline and 3.5 ml of triethylamine there is obtained O-2,4-dichlorophenyl-N-thiazolinyl-2-chloromethylphosphonamidothioate at the yield of 32.2%, melting point 145°–146° C.

Found, %: N 7.19, 7.06; P 8.11, 8.12. $C_{10}H_{10}Cl_3N_2OPS_2$. Calculated, %: N 7.46; P 8.25.

EXAMPLE 8

O-ethyl-N-thiazolinyl-2-methylphosphonamidothioate

In a manner similar to that described in Example 1 hereinbefore, from 4.7 g of O-ethylmethylthiophosphonic chloride, 3 g of 2-aminothiazoline and 4.1 ml of triethylamine there is obtained O-ethyl-N-thiazolinyl-2-methylphosphonamidothioate at the yield of 68%, melting point of 104°–105° C.

Found, %: P 14.10, 13.95; S 28.18, 28.39. $C_6H_{13}N_2OPS_2$. Calculated, %: P 13.81; S 28.59.

EXAMPLE 9

O-4-chlorophenyl-N-thiazolinyl-2-methylphosphonamidothioate

In a manner similar to that described in the foregoing Example 1, from 6.2 g of O-4-chlorophenylmethylthiophosphonic chloride, 2.8 g of 2-aminothiazoline and 3.8 ml of triethylamine there is obtained O-4-chlorophenyl-N-thiazolinyl-2-methylphosphonamidothioate at the yield of 34%, melting point of 130°–131° C.

Found, %: P 9.62; S 20.85. $C_{10}H_{12}ClN_2OPS_2$. Calculated, %: P 10.09; S 20.91.

EXAMPLE 10

O-4-chlorophenyl-N-thiazolyl-2-methylphosphonamidothioate

To a solution of 1.9 g of 2-aminothiazole and 3 ml of triethylamine in 200 ml of benzene there are dropwise added, at the temperature of from 10° to 15° C., 4.5 g of O-4-chlorophenylmethylthiophosphonic chloride. The mixture is heated at reflux for 5 hours and the precipitate is filtered off. The filtrate is evaporated in vacuum. The resulting oil is subjected to chromatography using a silica gel-packed column. Using a mixture of acetone with hexane in the ratio of 1:20 first eluted is N,N'-bis-(4-chlorophenoxymethylthiophosphinyl)-imonothiazoline at the yield of 6.3%, melting point of 133°–134° C.

Found, %: Cl 13.74, 13.73; N 5.32, 5.23; P 12.35, 11.77. $C_{17}H_{16}Cl_2N_2O_2P_2S_3$. Calculated, %: Cl 13.92; N 5.50; P 12.16.

Thereafter, eluted is O-4-chlorophenyl-N-thiazolyl-2-methylphosphonamidothioate at the yield of 34.6%, melting point of 105°–106° C.

Found, %: N 9.11, 9.13; S 20.82, 20.88. $C_{10}H_{10}ClN_2OPS_2$. Calculated, %: N 9.19; S 21.04.

EXAMPLE 11

O-phenyl-N-thiazolyl-2-methylphosphonamidate

In a manner similar to that described in the foregoing Example 10, from 2.0 g of 2-aminothiazole, 3.81 g of O-phenylmethylphosphonic chloride and 2.02 g of triethylamine there is obtained O-phenyl-N-thiazolyl-2-methylphosphonamidate at the yield of 38%; melting point 83°–85° C.

Found, %: N 9.58, 9.63; P 10.31, 10.40; S 10.66, 10.95. $C_{10}H_{10}ClN_2O_2PS$. Calculated, %: N 9.70; P 10.73; S 11.11.

EXAMPLE 12

O-ethyl-N-thiazolinyl-2-methylphosphonamidate

In a manner similar to that described in Example 1 hereinbefore, from 4.08 g of 2-aminothiazoline, 5.70 g of O-ethylmethylphosphonic chloride and 4.04 g of triethylamine there is obtained O-ethyl-N-thiazolinyl-2- methylphosphonamidate with a quantitative yield; melting point is 114°–115° C.

Found, %: N 12.45, 12.48; S 13.98, 14.14. $C_8H_{15}N_2O_3PS$. Calculated, %: N 12.38; S 14.17.

EXAMPLE 13

O-methyl-O-phenyl-N-thiazolinyl-2-phosphamidothioate

In a manner similar to that described in Example 1 hereinbefore, from 3.06 g of 2-aminothiazoline, 6.7 g of O-methyl-O-phenyl-chlorothiophosphate and 3.03 g of triethylamine there is obtained O-methyl-O-phenyl-N-thiazolinyl-2-amidophosphate at the yield of 5%, melting point of 164°–165° C.

Found, %: N 9.70, 9.60; P 10.67, 10.87; S 22.38, 22.49. $C_{10}H_{13}N_2O_2PS_2$. Calculated, %: N 9.72; P 10.74; S 22.24.

EXAMPLE 14

N,N-diethylamido-N'-thiazolinyl-2-methylphosphonamidate

In a manner similar to that described in Example 1 hereinbefore, from 3.06 g of 2-aminothiazoline, 5.10 g of N,N-diethylmethylphosphonamidic chloride and 3.03 g of triethylamine there is obtained N,N-diethyl-N'-thiazolinyl-2-methylphosphondiamidate in the form of an oil with the yield of 74%. Treatment of the oil with an alcoholic solution of picric acid results in picrate of N,N-diethyl-N-thiazolinyl-2-methylphosphondiamidate with the melting point of 102° C.

Found, %: N 17.90, 17.80; S 7.04. $C_8H_{18}N_3OPS$. Calculated, %: N 18.10; S 6.90.

EXAMPLE 15

N,N'-bis-(thiazolinyl-2-amido)-methylphosphonate

To 5.5 g of 2-aminothiazoline and 7.5 ml of triethylamine there are added 3.7 g of methylthiophosphonic chloride. The mixture is stirred for 30 minutes, whereafter 100 ml of chloroform are added thereto. Upon maturation of the solution crystals of N,N-bis-(thiazolinyl-2-amido)-methylphosphonate are precipitated therefrom. Yield is 28%, melting point 152°–154° C.

Found, %: N 21.06; P 11.55; S 23.20, 23.13. $C_7H_{13}N_4OPS_2$. Calculated, %: N 21.20; P 11.71; S 24.26.

EXAMPLE 16

Wettable powder 25 parts by weight of a compound of formula (1), 10 parts by weight of a mixture of alkylaryl esters of polyethylene glycol, 5 parts by weight of alcohol-sulphite slops and 60 parts by weight of kaoline are intermixed until a homogeneous mixture is formed which is then employed in the form of an aqueous slurry.

Granules 10 parts by weight of a compound of formula (1) are dissolved in acetone, added with 90 parts by weight of silica, intermixed, whereafter acetone is removed from the mixture.

Solutions

A compound of formula (1) in an amount ranging from 1 to 20 parts by weight is dissolved in 99–80 parts by weight of an appropriate solvent (water, acetone, alcohol and the like) and the thus-prepared solution is ready for use.

EXAMPLE 17

Insecticidal and acaricidal effects (a) Effect against housefly (*Musca domestica L.*)

Solutions of compounds of formula (1) in acetone (0.5 mcl) are locally applied onto prothorax of housefly. Evaluation of the killed insects is performed after 24 hours.

(b) Effect against rice weevil (*Calandra oryzae L.*)

Rice weevil beetles are sprayed with aqueous or aquo-alcoholic solutions of a compound of formula (1). The liquid application rate is 35 ml/m². Evaluation of the number of killed beetles is performed after 48 hours.

(c) Effect against Graphosoma bugs (*Graphosoma semipunetamum*)

Onto sternites of mediorax of adult bugs drops of solutions of compounds of formula (1) in acetone are applied in the volume of 1.1 mcl. Evaluation of the number of killed bugs is performed after 24 hours.

(d) Effect against Colorado potato beetle (*Leptinotarsa decemlineata say.*)

Drops of solution of formula (1) compounds in acetone in the volume of 3.3 mcl are applied onto vetral surface of the beetles. Evaluation of the number of killed beetles is performed after 24 hours.

(e) Effect against mosquito grubs (*Culex pipiens moletus F.*)

To determine toxicity of the compounds corresponding to formula (1), mosquito grubs are placed into test solutions containing certain concentrations of the compounds. Number of killed grubs is evaluated after 24 hours.

(f) Effect against web ticks (*Tetranychus articae koch*)

Bean leaves infected with web ticks are placed for 1–2 seconds into solutions of formula (1) compounds in acetone (to determine the total acaricidal power) or upper surface of the leaves is wetted (to determine transepidermal acaricidal power).

Shown in Tables 1 and 2 are values of $LD_{50}$ of the tested compounds of formula (1).

EXAMPLE 18

Systematic effect of O-phenyl-N-thiazolinylamidomethylphosphonate against lucerne aphid (*Pergandeida medicaginis Koch.*)

10% granulated compositions (Example 16) are introduced into soil at the rate of 1.2–3 kg/ha.

Experiments show that the composition according to the present invention features a systematic effect against cotton aphid, protects cotton for 10 days and, in its effect, is superior over dimethoate.

EXAMPLE 19

Herbicidal effect

Tests for herbicidal activity of compounds corresponding to formula (1) are conducted under laboratory conditions according to the following procedure.

Test plants, i.e. wheat, oats, millet, garden radish, are grown on an agar medium for 7 days under thermostat conditions. Introduced into the agar medium are aqueous slurries of compounds of formula (1) prepared from 25% wettable powders (Example 16) in doses ranging from 0.04 to 1 kg/ha.

The efficacy of the herbicides is determined by way of measuring length of radicles and roots of the plants.

As the control use is made of plants grown on a pure (without herbicide) agar medium. Evaluated are doses of the compositions resulting in a 50% inhibition of the plant growth.

Preliminary tests have shown that millet and oats are especially sensitive to the test compounds. The test results are shown in Table 3 hereinbelow.

Table 1

Comparative toxicity (LD$_{50}$) of formula (1) compounds for harmful insects and ticks

| Compounds | Graphosoma bugs | Housefly | Rice weevil | Colorado beetle | Mosquito grubs | Web tick Acaricidal Power Total | Transepidermal |
|---|---|---|---|---|---|---|---|
| ![structure: O=P(CH3)(OC6H5)-NH-C(=N)S (thiazoline)] | 0.05 | 0.01 | 0.06 | 0.04 | $1 \cdot 10^{-5}$ | 0.002 | 0.02 |
| ![structure: S=P(CH3)(OC6H3Cl2-2,4)-NH-C(=N)S] | 0.10 | 0.25 | 0.23 | 0.10 | $2 \cdot 10^{-7}$ | 0.023 | 0.10 |
| malathione (conventional) | — | 0.20 | — | — | $1 \cdot 10^{-2}$ | — | — |
| chlorophos (conventional) | — | 0.04 | 0.07 | 0.12 | — | — | — |
| bitex (conventional) | — | — | — | — | $3 \cdot 10^{-7}$ | — | — |
| basudine (conventional) | 0.1 | — | — | 0.08 | $5 \cdot 10^{-2}$ | — | — |

| 1 | 2 | 3 | 4 | 5 | 6 | 7 | 8 |
|---|---|---|---|---|---|---|---|
| Gardona (conventional) | 0.12 | 0.02 | — | — | $8 \cdot 10^{-2}$ | — | — |
| valexone (conventional) | 0.04 | — | — | — | $9 \cdot 10^{-7}$ | — | — |
| Galecrone (conventional) | — | — | — | 0.15 | — | 0.005 | 0.4 |
| Phenitrothione (conventional) | — | — | — | 0.25 | $7 \cdot 10^{-7}$ | — | — |
| Bensophosphate (conventional) | — | 0.07 | — | 0.12 | — | — | — |
| Tetradiphone (conventional) | — | — | — | — | — | 2 | 10 |
| menasone (conventional) | | | | | | 0.02 | |
| ovotrame (conventional) | | | | | | 0.003 | 10 |

Table 2

Comparative toxicity of formula (1) compounds for harmful insects

| Compounds | LD$_{50}$ Graphosoma bugs | Colorado beetle | Mosquito grubs |
|---|---|---|---|
| ![structure: S=P(CH3)(OC6H2Cl3-2,4,5)-NH-C(=N)S] | 0.1 | 0.014 (0.01–0.02) | $3.2 \times 10^{7}$ ($2.7 \times 10^{-7}$–$3.8 \times 10^{-7}$) |
| ![structure: S=P(ClCH2)(OC6H3Cl2-2,4)-NH-C(=N)S] | — | — | $8.1 \times 10^{-6}$ ($6.8 \times 10^{6}$–$9.6 \times 10^{-6}$) |
| ![structure: S=P(CH3)(OC6H3Cl2-2,4)-NH-C(=N)S] | — | — | $2.5 \times 10^{-7}$ ($2.1 \times 10^{-7}$–$2.9 \times 10^{-7}$) |
| ![structure: O=P(CH3)(OC6H5)-NH-C(=N)S] | 0.05 | 0.027 (0.020–0.039) | $6.5 \times 10^{-5}$ ($3.8 \times 10^{5}$–$8.0 \times 10^{-5}$) |
| ![structure: O=P(CH3)(OC6H4Cl-4)-NH-C(=N)S] | 0.1 | 0.1 | $1 \times 10^{-5}$ |

Table 2-continued
Comparative toxicity of formula (1) compounds for harmful insects

| Compounds | LD$_{50}$ | | |
|---|---|---|---|
| | Graphosoma bugs | Colorado beetle | Mosquito grubs |
| S=P(OC$_6$H$_4$Cl-4)(CH$_3$)-NH-C(=N-)(-S-) [thiazoline] | 0.1 | 0.056 | $1.4 \times 10^{-6}$ ($1.2 \times 10^{-6}$–$1.6 \times 10^{-6}$) |

| 1 | 2 | 3 | 4 |
|---|---|---|---|
| O=P(OC$_2$H$_5$)(CH$_3$)-NH-C(=N-)(-S-) | — | — | $1 \times 10^{-5}$ |
| O=P(OC$_6$H$_3$Cl$_2$-2,4)(CH$_3$)-NH-C(=N-)(-S-) | — | — | $1 \times 10^{-5}$ |
| Dilor (conventional) | — | 0.022 (0.017–0.029) | — |
| Chlorophos (Conventional) | 0.025 | 0.14 (0.11–0.17) | $2.5 \times 10^{-6}$ ($2.1 \times 10^{-6}$–$2.9 \times 10^{-6}$) |
| Valexon (Conventional) | — | — | $4.2 \times 10^{-7}$ ($3.3 \times 10^{-7}$–$5.2 \times 10^{-7}$) |

Table 3
Herbicidal activity of compounds
Compound dose (kg/ha) ensuring 50% inhibition of the plant growth

| Compounds | wheat | | oats | | millet | | radish | |
|---|---|---|---|---|---|---|---|---|
| | Radicals | Roots | Radicals | Roots | Radicals | Roots | Radicals | Roots |
| 1 | 2 | 3 | 4 | 5 | 6 | 7 | 8 | 9 |
| CH$_3$, C$_6$H$_5$O — P(=O)—NH—C(=N-)(-S-) | 1 | 1 | 0.09 | 0.06 | 0.04 | 0.1 | 1 | 1 |
| CH$_3$, 4-ClC$_6$H$_4$O — P(=S)—NH—C(=N-)(-S-) | 1 | 1 | 0.09 | 0.3 | 0.05 | 1 | 1 | 1 |
| CH$_3$, 4-ClC$_6$H$_4$O — P(=O)—NH—C(=N-)(-S-) | 1 | 1 | 0.08 | 0.04 | 0.05 | 0.1 | 1 | 1 |
| CH$_3$, 2,4-Cl$_2$C$_6$H$_3$O — P(=S)—NH—C(=N-)(-S-) | 1 | 1 | 1 | 1 | 0.05 | 1 | 1 | 1 |
| CH$_3$, 2,4,5-Cl$_3$C$_6$H$_2$O — P(=S)—NH—C(=N-)(-S-) | 1 | 1 | 0.08–0.05 | | 0.04–0.5 | | 1 | 1 |
| ClCH$_2$, 2,4-Cl$_2$C$_6$H$_3$O — P(=S)—NH—C(=N-)(-S-) | 1 | 1 | 0.09–0.07 | | 0.06–0.5 | | 1 | 1 |
| CH$_3$, C$_2$H$_5$O — P(=O)—NH—C(=N-)(-S-) | 1 | 1 | 1 | 1 | 1 | 1 | 1 | 1 |

Table 3-continued

| Compounds 1 | Herbicidal activity of compounds Compound dose (kg/ha) ensuring 50% inhibition of the plant growth | | | | | | | |
|---|---|---|---|---|---|---|---|---|
| | wheat | | oats | | millet | | radish | |
| | Radicals 2 | Roots 3 | Radicals 4 | Roots 5 | Radicals 6 | Roots 7 | Radicals 8 | Roots 9 |
| CH₃, O \\ ‖ P—NH—C(=N, S—) / 4-Cl C₆H₄O | 1 | 1 | 1 | 1 | 1 | 1 | 1 | 0.6 |
| CH₃, O \\ ‖ P—NH—C(=N, S—) / 2,4-Cl₂C₆H₃O | 1 | 1 | 1 | 1 | 1 | 1 | 1 | 0.9 |
| CH₃O, O \\ ‖ P—NH—C(=N, S—) / C₆H₅O | 1 | 1 | 1 | 1 | 1 | 1 | 1 | 1 |
| CH₃, O \\ ‖ P—NH—C(=N, S—) / (C₂H₅)₂N | 1 | 1 | 1 | 1 | 1 | 1 | 1 | 1 |
| CH₃, S \\ ‖ P—NH—C(=N, S—) / C₂H₅O | 1 | 1 | 1 | 1 | 1 | 1 | 1 | 1 |

What is claimed is:

1. O-phenyl-N-thiazolinyl-2-methylphosphonamidate.

2. O-phenyl-N-thiazolinyl-2-methylphosphonamidothioate.

3. A composition according to claim 1, containing as an active principle O-phenyl-N-thiazolinyl-2-methylphosphonamidate.

4. A composition according to claim 1, containing as an active principle O-phenyl-N-thiazolinyl-2-methylphosphonamidothioate.

5. An insecticidal and acaricidal composition containing, as an active principle, a compound selected from the group consisting of O-phenyl-N-thiazolinyl-2-methylphosphonamidate and O-phenyl-N-thiazolinyl-2-methylphosphonamidothioate, and an inert carrier therefor.

* * * * *